United States Patent [19]

Maier et al.

[11] 4,048,306

[45] Sept. 13, 1977

[54] ALDEHYDE-ERYTHROMYCYLAMINE CONDENSATION PRODUCTS

[75] Inventors: Roland Maier; Eberhard Woitun; Bernd Wetzel, all of Biberach; Wolfgang Reuter, Laupertshausen; Hanns Goeth, Biberach; Uwe Lechner, Ummendorf, all of Germany

[73] Assignee: Boehringer Ingelheim GmbH, Ingelheim am Rhein, Germany

[21] Appl. No.: 671,421

[22] Filed: Mar. 29, 1976

[30] Foreign Application Priority Data

Apr. 7, 1975 Germany .............................. 2515075
Feb. 14, 1976 Germany .............................. 2606030

[51] Int. Cl.² ............................................. A61K 31/70

[52] U.S. Cl. ......................................... 424/180; 536/9
[58] Field of Search ................... 260/210 E; 424/180; 536/9

[56] References Cited

U.S. PATENT DOCUMENTS 3,660,376   5/1972   Massey ............................. 260/210 E

*Primary Examiner*—Lewis Gotts
*Assistant Examiner*—Cary Owens
*Attorney, Agent, or Firm*—Hammond & Littell

[57] ABSTRACT

The invention relates to novel erythromycin derivatives, and non-toxic, pharmacologically acceptable acid addition salts thereof. The compounds as well as the salts are useful as antibacterials.

13 Claims, No Drawings

ALDEHYDE-ERYTHROMYCYLAMINE CONDENSATION PRODUCTS

This invention relates to novel erythromycin derivatives, as well as to methods of preparing these compounds.

More particularly, the present invention relates to novel condensation products of aldehydes and erythromycylamine represented by the formulas

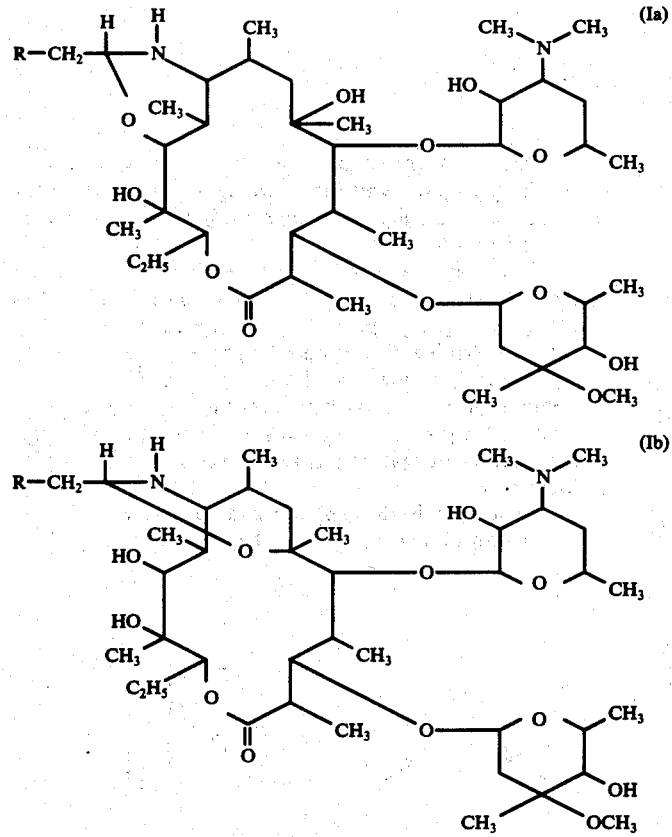

wherein R is hydroxyl; phenoxy; phenyl-(alkoxy of 1 to 3 carbon atoms); alkoxy of 1 to 4 carbon atoms; hydroxy-(alkoxy of 1 to 4 carbon atoms); (alkoxy of 1 to 3 atoms)-(alkoxy of 1 to 4 carbon atoms); di(alkyl of 1 to 3 carbon atoms)amino-(alkoxy of 1 to 4 carbon atoms); (alkoxy of 1 to 3 carbon atoms)-carbonyl-(alkoxy of 1 to 4 carbon atoms); mercapto; phenylmercapto, where the phenyl moiety is unsubstituted or methyl-, methoxy-, ethoxy-, isopropoxy- or propoxy-substituted; phenyl-(alkyl of 1 to 3 carbon atoms)-mercapto; (straight or branched alkyl of 1 to 5 carbon atoms)-mercapto; cyclohexyl-mercapto; hydroxy-(alkyl of 1 to 3 carbon atoms)-mercapto; di(alkyl of 1 to 3 carbon atoms)amino-(alkyl of 1 to 3 carbon atoms)-mercapto; (alkoxy of 1 to 3 carbon atoms)-carbonyl-(alkyl of 1 to 3 carbon atoms)-mercapto; cyano-(alkyl of 1 to 3 carbon atoms)-mercapto; —NR$_2$R$_3$, where R$_2$ and R$_3$, which may be identical to or different from each other, are each hydrogen, phenyl, phenyl-(alkyl of 1 to 3 carbon atoms), alkyl of 1 to 4 carbon atoms or, together with each other and the nitrogen atom to which they are attached, a 5- to 6-membered monocyclic heterocylic ring which may contain an oxygen, sulfur or additional nitrogen atom;

$$-O-\overset{\overset{O}{\|}}{C}-R_4,$$

where R$_4$ is straight or branched alkyl of 1 to 5 carbon atoms, benzyl or phenyl; —NH—CO—R$_5$, where R$_5$ is straight or branched alkyl of 1 to 5 carbon atoms, mono- or di- halo-substituted-(alkyl of 1 to 5 carbon atoms), cyano-(alkyl of 1 to 5 carbon atoms), phenyl-(alkyl of 1 to 3 carbon atoms) where the phenyl moiety may be mono- or di- or trimethoxy- or mono- or di-halo-substituted and the alkyl moiety may be monohalosubstituted, phenoxy-(alkyl of 1 to 3 carbon atoms), phenyl-(alkenyl of 2 to 4 carbon atoms), phenyl or phenyl having one or more methyl, hydroxyl, methoxy, nitro or chloro substitutents attached thereto, or R$_5$ is pyridyl; furyl; fluoro-furyl; thienyl; N-phenyl-carbamoyl;

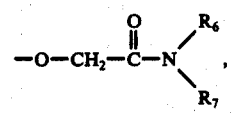

where R$_6$ and R$_7$, which may be identical to or different from each other, are each methyl, ethyl, propyl or isopropyl;

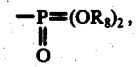

where R$_8$ is straight or branched alkyl of 1 to 5 carbon atoms; —NH—SO$_2$—R$_9$, where R$_9$ is alkyl of 1 to 4 carbon atoms or phenyl or (alkyl of 1 to 3 carbon atoms)- phenyl; or —SO$_2$—R$_{10}$, where R$_{10}$ is alkyl of 1 to 3 carbon atoms or phenyl or (alkyl of 1 to 3 carbon atoms)-phenyl;

and non-toxic, pharmacologically acceptable acid addition salts thereof.

The compounds embraced by formulas I, Ia and Ib may be prepared by the following methods:

METHOD A

By reacting erythromycylamine of the formula (II)

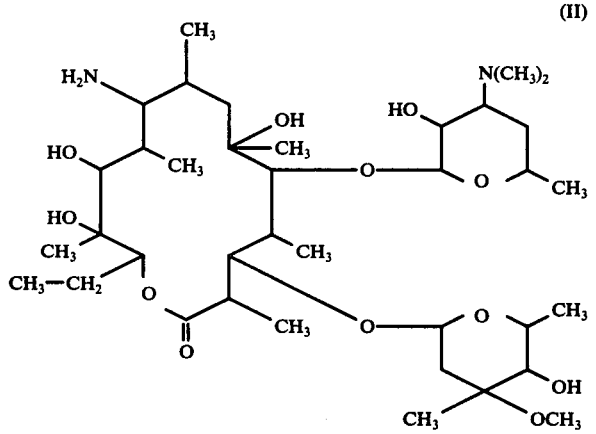

with an aldehyde of the formula (III)

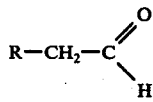

wherein R has the same meanings as in formulas I, Ia and Ib.

The reaction is preferably carried out in the presence of a solvent or a suspension agent at a temperature between 0° and 150° C. Preferred examples of suitable solvents or suspension agents are polar solvents, such as water, alcohols, dioxane, dimethylformamide, dimethylsulfoxide or mixtures of any two or more of these.

It is of advantage for the performance of the reaction if the aldehyde of the formula III is liberated in situ from a suitable precursor. Preferred precursors are acetals of the formula

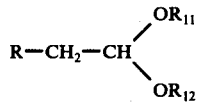
(IV)

wherein R has the meanings previously defined, and R$_{11}$ and R$_{12}$, which may be identical to or different from each other, are lower alkyl or, together with each other and the grouping

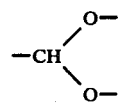

to which they are attached, a 5- to 7-membered ring.

Acids, especially acid ion exchangers, are suitable for liberating an aldehyde of the formula III from an acetal of the formula IV.

If R in formula III or IV is free or mono-substituted amino, this amino group should be provided with a protective group prior to the reaction with erythromycylamine; the protective group is then removed again after completion of the reaction. Examples of suitable protective groups are those conventionally used for the protection of aminoacids in peptide chemistry, such as benzyl, triphenylmethyl or carbobenzoxy.

Method B

By catalytic hydrogenation and simultaneous decarboxylation of a compound of the formula (V)

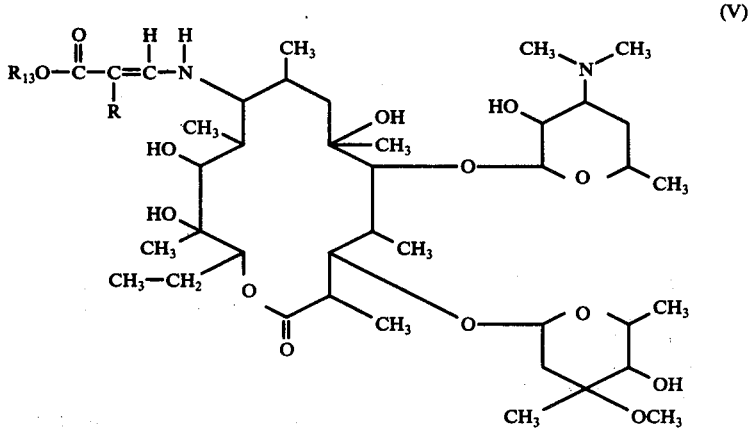

wherein R has the meanings previously defined, and R$_{13}$ is a substituent which is readily split off by hydrogenation, such as benzyl, benzhydryl or triphenylmethyl.

The hydrogenation and simultaneous decarboxylation are advantageously carried out in the presence of an organic solvent at a temperature between 0° and 150° C, preferably however, at room temperature. Examples of preferred suitable solvents are polar organic solvents, such as alcohols, esters or dioxane. Suitable catalysts for the hydrogenation are especially noble metals, such as finely divided palladium or platinum.

The compounds represented by formulas I, Ia and Ib form acid addition salts with inorganic or organic acids. Examples of non-toxic, pharmacologically acceptable acid addition salts are those formed with hydrochloric acid, hydrobromic acid, sulfuric acid, acetic acid, citric acid, laurylsulfuric acid, 8-chlorotheophylline or the like.

It was not possible to ascribe any particular one of formulas I, Ia or Ib to the end products of methods A and B. In other words, it was not possible to determine whether any one particular end product had the tautomeric structure represented by formula I, Ia or Ib. Therefore, the nomenclature of the end products hereinbelow is in terms of the condensation product of erythromycylamine and the particular aldehyde which was used.

The starting compound erythromycylamine of the formula II is described in the literature. Its preparation is, for example, described in J. Med. Chem. 17, 105–107 (1974). The aldehydes and acetals of the formulas III and IV are also described in the literature, or they may be prepared by methods described in the literature.

The starting compounds of the formula V may be obtained by reacting erythromycylamine with an unsaturated carboxylic acid ester of the formula

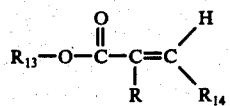
(VI)

wherein R and $R_{13}$ have the meanings previously defined, and $R_{14}$ is hydroxyl, alkoxy or dialkylamino. The reaction is carried out in the presence of an organic suspension agent or solvent at a temperature between 0° and 150° C, preferably between 20° and 120° C. Examples of suitable solvents or suspension agents are alkanols, such as ethanol; dioxane; dimethylformamide; dimethylsulfoxide; or mixtures of any two or more of these.

The unsaturated carboxylic acid esters of the formula VI wherein $R_{14}$ is hydroxyl may be obtained by condensation of an acetate of the formula

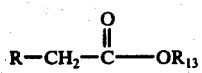
(VII)

wherein R and $R_{13}$ have the meanings previously defined, with a formic acid ester in the presence of a basic condensation agent, such as an alkali metal, an alkali metal hydride or an alkali metal alcoholate.

The enols thus obtained may optionally be converted into compounds of the formula VI wherein $R_{14}$ is alkoxy or dialkylamino by means of an alkylating agent, such as diazomethane, or by reaction with a dialkylamine.

The following examples illustrate the present invention and will enable others skilled in the art to understand it more completely. It should be understood, however, that the invention is not limited solely to the particular examples given below.

PREPARATION OF STARTING COMPOUNDS

EXAMPLE A

N-(2-Methoxy-2-carbobenzyloxy)-vinyl-erthromycylamine

A mixture consisting of 1.2 gm (0.0062 mol) of benzyl 1-methoxy-2-hydroxy-acrylate, 3.6 gm (0.005 mol) of erythromycylamine and 20 ml of dioxane was allowed to stand at room temperature for 2 hours. The mixture was then diluted with 100 ml of ether, washed twice with 25 ml of 1 N sodium hydroxide and once with water, dried with magnesium sulfate, and the solvent was evaporated. The residue was purified by column chromatography (basic aluminum oxide; chloroform/methanol = 40:1), yielding 3 gm of a colorless amorphous powder, m.p. 179° C.

The following compounds were obtained in analogous manner:

a. N-(2-Dimethylamino-2-carbobenzyloxy)-vinyl-erythromycylamine, m.p. 135° C, from benzyl 1-dimethylamino-2-hydroxyacrylate and erythromycylamine.

b. N-(2-Morpholino-2-carbobenzyloxy)-vinyl-erythromycylamine, m.p. 135°–137° C, from benzyl 1-morpholino-2-hydroxy-acrylate and erythromycylamine.

c. N-(2-Phenoxy-2-carbobenzyloxy)-venyl-erythromycylamine, m.p. 110° C, from benzyl 1-phenoxy-2-hydroxy-acrylate and erythromycylamine.

d. N-[2-(2-Dimethylamino)-ethoxy-2-carbobenzyloxy]-vinylerythromycylamine, m.p. 100°–105° C, from benzyl 1-(2-dimethylamino) -ethoxy-2-hydroxyacrylate and erythromycylamine.

e. N-[2-(2-(N'-o-methoxybenzoyl)-amino-2-carbobenzyloxy]- vinyl-erythromycylamine, m.p. 140°–144° C, from benzyl 1- [N-(p-methoxy)-benzoyl]-amino-2-hydroxy-acrylate and erythromycylamine.

f. [2-(N'-acetyl)-amino-2-carbobenzyloxy]-vinyl-erythromycylamine, m.p. 125-131° C, from benzyl 1-(N-acetyl)-amino-2-hydroxy-acrylate and erythromycylamine.

EXAMPLE B

Benzyl 1-methoxy-2-hydroxy-acrylate

A solution of 8.4 gm (0.05 mol) of benzyl methoxyacetate and 7.5 gm (0.055 mol) of benzyl formate in 10 ml of absolute toluene was added dropwise over a period of 1.5 hours to a mixture of 1.15 gm (0.05 mol) of sodium dust and 50 ml of absolute toluene at room temperature, while vigorously stirring. The resulting clear solution was diluted with 80 ml of ether, and the organic phase was extracted with 100 ml of water. The aqueous phase was extracted three times with 30 ml of ether at pH 5 and 7, and the extracts at pH 5 were discarded. 1.2 gm of a colorless oil were obtained from the extracts at pH 7. $R_f$ 0.3 (silicagel; chloroform/methanol = 40:1)

The following compounds were obtained in analogous manner:

a. Benzyl-1-dimethylamino-2-hydroxy-acrylate, a weakly yellow oil; $R_f$ 0.7 (silicagel; ethanol); from benzyl dimethylamino-acetate and benzyl formate.

b. Benzyl 1-morpholino-2-hydroxy-acrylate, m.p. 109°–110° C, from benzyl morpholino-acetate and benzyl formate.

c. Benzyl 1-phenoxy-2-hydroxy-acrylate, a yellow oil, from benzyl phenoxy-acetate and benzyl formate.

d. Benzyl 1-(2-dimethylamino)-ethoxy-2-hydroxy-acrylate, a brown oil, from ethyl 2-dimethylamino-acetate and benzyl formate.

e. Benzyl 1-(o-methoxybenzoyl)-amino-2-hydroxy-acrylate, m.p. 67°–69° C, from benzyl o-methoxybenzoylamino-acetate and benzyl formate.

f. Benzyl 1-acetylamino-2-hydroxy-acrylate, an oil, $R_f$: 0.2 (silicagel; chloroform/methanol = 13:1), from benzyl acetylamino-acetate and benzyl formate.

PREPARATION OF END PRODUCTS

EXAMPLE 1

Methoxyacetaldehyde-erythromcylamine condensation product by method B 1 gm of N-(2-methoxy-2-carbobenzyloxy)-vinyl-erythromycylamine was hydrogenated in a mixture of 15 ml of tert. butanol and 3 ml of ethyl acetate in the presence of 0.5 gm of 20% palladium-on-charcoal in a shaking vessel for 3 hours. Subsequently, the catalyst was filtered off, and the filtrate was evaporated. The residue was taken up in ether, filtered, and the filtrate was mixed with petroleum ether. 600 gm (85% of theory) of a white powder, m.p. 191° C, were obtained.

Elemental analysis: $C_{40}H_{74}N_2O_{13}$; (791.05).

Calculated: C, 60.73%; H, 9.43%; N, 3.54% . Found: C, 60.70%; H, 9.43%; N, 3.61% .

The hydrochloride of the free base began to decompose above 193° C; the lauryl sulfate had a m.p. of 132° C.

The following compounds were obtained in analogous manner:

a. Dimethylaminoacetaldehyde-erythromycylamine condensation product, m.p. 141° C, from N-(2-dimethylamino-2-carbobenzyloxy)-vinyl-erythromycylamine.

b. Morpholinoacetaldehyde-erythromycylamine condensation product, m.p. 141° C, from N-(2-morpholino-2-carbobenzyloxy)-vinyl-erythromycylamine.

c. Phenoxyacetaldehyde-erythromycylamine condensation product, m.p. 115°–120° C, from N-(2-phenoxy-2-carbobenzyloxy) -vinyl-erythromycylamine.

d. 2-Dimethylaminoethoxyacetaldehyde-erythromycylamine condensation product, m.p. 160°–165° C, from N-[2-(2-dimethylamino)-ethoxy-2-carbobenzyloxy]-vinyl-erythromycylamine.

e. (o-Methoxybenzoyl)-aminoacetaldehyde-erythromycylamine condensation product, m.p. 148°–150° C, from N-[2-(N'-o- methoxybenzoyl)-amino-2-carbobenzyloxy]-vinyl-erythromycylamine.

f. Acetylaminoacetaldehyde-erythromycylamine condensation product, m.p. 143°–147° C, from N-[2-(N'-acetyl)-amino-2-carbobenzyloxy]-vinyl-erythromycylamine.

EXAMPLE 2

Glycolaldehyde-erythromycylamine condensation product by method A 42 gm of erythromycylamine and 4.2 gm of glycolaldehyde were stirred in 600 ml of absolute ethanol at room temperature for 24 hours. After evaporation of the ethanol, the residue was taken up in 500 ml of hot acetonitrile. Upon cooling, 35 gm of colorless crystals precipitated, which were dried at 80° C in vacuo. M.p. 210°–215° C (decomp.).

Elemental analysis: $C_{39}H_{72}N_2O_{13}$; (777.0).

Calculated: C, 60.30%; H, 9.35%; N, 3.61%.
Found: C, 60.00%; H, 9.32%; N, 3.58%.

The following compounds were prepared in analogous manner:

a. n-Butoxyacetaldehyde-erythromycylamine condensation product, m.p. 92°–96° C (decomp.).

b. Benzyloxyacetaldehyde-erythromycylamine condensation product, m.p. 96°–100° C (decomp.).

c. Phenoxyacetaldehyde-erythromycylamine condensation product, m.p. 116°–122° C (decomp.).

d. Methylsulfonylacetaldehyde-erythromycylamine condensation product, m.p. 179° C (decomp.)

e. p-Tolylsulfonylacetaldehyde-erythromycylamine condensation product, m.p. 158° C (decomp.).

f. N-(benzoyl)-aminoacetaldehyde-erythromycylamine condensation product, m.p. 148°–153° C (decomp.).

g. N-(p-Methoxybenzoyl)-aminoacetaldehyde-erythromycylamine condensation product, m.p. 148°–150° C (decomp.).

h. N-(o-Chlorobenzoyl)-aminoacetaldehyde-erythromycylamine condensation product, m.p. 150°–160° C (decomp.).

i. N-(o-Toluyl)-aminoacetaldehyde-erythromycylamine condensation product, m.p. 145°–148° C (decomp.).

k. N-(Phenylacetyl)-aminoacetaldehyde-erythromycylamine condensation product, m.p. 132°–138° C (decomp.).

l. Dibutylaminoacetaldehyde-erythromycylamine condensation product, m.p. 123°–128° C (decomp.).

m. Pyrrolidinoacetaldehyde-erythromylcylamine condensation product, m.p. 129°–132° C (decomp.).

n. Piperidinoacetaldehyde-erythromycylamine condensation product, m.p. 120°–125° C (decomp.).

o. N-Benzyl-N-methyl)-aminoacetaldehyde-erythromycylamine condensation product, m.p. 118°–121° C (decomp.).

p. Methylaminoacetaldehyde-erythromycylamine condensation product, m.p. 134°–137° C (decomp.).

q. N-(2-Chloroacetyl)-aminoacetaldehyde-erythromycylamine condensation product, m.p. 195°–200° C (decomp.).

r. N-(2,2-Dichloroacetyl)-aminoacetaldehyde-erythromycylamine condensation product, m.p. 144°–148° C (decomp.).

s. N-(2-Cyanoacetyl)-aminoacetaldehyde-erythromycylamine condensation product, m.p. 174°–178° C (decomp.).

t. N-(Caproyl)-aminoacetaldehyde-erythromycylamine condensation product, m.p. 125°–130° C (decomp.).

u. N-([2-Bromo-2-phenyl]-acetyl)-aminoacetaldehyde-erythromycylamine condensation product, m.p. 117°–121° C (decomp.).

v. N-(2-Phenoxyacetyl)-aminoacetaldehyde-erythromycylamine condensation product, m.p. 120°–125° C (decomp.).

w. N-(2-[o-Chlorophenyl]-acetyl)-aminoacetaldehyde-erythromycylamine condensation product, m.p. 135°–140° C (decomp.).

x. N-(2-[o,o'-Dichlorophenyl]-acetyl)-aminoacetaldehyde-erythromycylamine condensation product, m.p. 132°–136° C (decomp.).

y. N-(2-[p-Methoxyphenyl]-acetyl)-aminoacetaldehyde-erythromycylamine condensation product, m.p. 138°–145° C (decomp.).

z. N-(o,o'-Dimethoxybenzoyl)-aminoacetaldehyde-erythromycylamine condensation product, m.p. 145°–150° C (decomp.).

aa. N-(m,m'p-Trimethoxybenzoyl)-aminoacetaldehyde-erythromycylamine condensation product, m.p. 184°–186° C (decomp.).

bb. N-(p-Methoxybenzoyl)-aminoacetaldehyde-erythromycylamine condensation product, m.p. 140°-145° C (decomp.).

cc. N-(p-Toluyl)-aminoacetaldehyde-erythromycylamine condensation product, m.p. 150°-155° C (decomp.).

dd. N-(p-Nitrobenzoyl)-aminoacetaldehyde-erythromycylamine condensation product, m.p. 148°-150° C (decomp.).

ee. N-(2-Fluorofuroyl)-aminoacetaldehyde-erythromycylamine condensation product, m.p. 134°-138° C (decomp.).

ff. N-(2-Thienoyl)-aminoacetaldehyde-erythromycylamine condensation product, m.p. 150°-152° C (decomp.).

gg. N-(Nicotinoyl)-aminoacetaldehyde-erythromycylamine condensation product, m.p. 154°-156° C (decomp.).

hh. N-(Cinnamoyl)-aminoacetaldehyde-erythromycylamine condensation product, m.p. 150° C (decomp.).

ii. N-(o-Hydroxybenzoyl)-aminoacetaldehyde-erythromycylamine condensation product, m.p. 220°-223° C (decomp.).

jj. N-(p-Tolylsulfonyl)-aminoacetaldehyde-erythromycylamine condensation product, m.p. 143°-149° C (decomp.).

kk. N-(methylsulfonyl)-aminoacetaldehyde-erythromycylamine condensation product, m.p. 135°-140° C (decomp.).

ll. Propionylaminoacetaldehyde-erythromycylamine condensation product, m.p. 137°-140° C (decomp.).

mm. Pivaloylaminoacetaldehyde-erythromycylamine condensation product, m.p. 122°-126° C (decomp.).

EXAMPLE 3

Methoxyacetaldehyde-erythromycylamine condensation product by method A 2.3 gm (0.03 mol) of erythromycylamine and 1.2 gm (0.01 mol) of methoxyacetaldehyde-dimethylacetal were stirred in 20 ml of dioxane and 2 ml of water with 12 gm of Dowex 50 W at room temperature. After 6 hours of stirring, the ion exchanger was filtered off and washed with dioxane. The filtrate was evaporated, and the residue was purified by column chromatography (basic aluminum oxide, activity stage 3; chloroform/methanol = 40:1). The fractions with $R_f = 0.6$ were evaporated and brought to crystallization by treatment with ether/petroleum ether. 0.8 gm (33% of theory) of colorless crystals, m.p. 191° C, were obtained.

Elemental analysis: $C_{40}H_{74}N_2O_{13}$; (791.05). Calculated: C, 60.73%; H, 9.43%; N, 3.54%. Found: C, 60.63%; H, 9.48%; N, 3.60.

The following compounds were prepared in analogous manner:

a. (2-Methoxy)-ethoxyacetaldehyde-erythromycylamine condensation product, m.p. 95°-100° C, from (2-methoxy)-ethoxyacetaldehyde-diethylacetal and erythromycylamine.

b. (2-Hydroxy)-ethoxyacetaldehyde-erythromycylamine condensation product, m.p. 95°-98° C, from (2-hydroxy)-ethoxyacetaldehyde-diethylacetal and erythromycylamine.

c. (Carbethoxy)-methoxyacetaldehyde-erythromycylamine condensation product, m.p. 105°-110° C, from (carbethoxy)-methoxyacetaldehyde-diethylacetal and erythromycylamine.

d. N-(Acetyl)-aminoacetaldehyde-erythromycylamine condensation product, m.p. 143°-147° C, from N-(acetyl)-aminoacetaldehyde-dimethylacetal and erythromycylamine.

EXAMPLE 4

Methylthioacetaldehyde-erythromycylamine condensation product 1.3 gm (0.008 mol) of methylthioacetaldehyde-diethylacetal were stirred at room temperature for 15 minutes in a mixture of 20 ml of dioxane and 4 ml of water with 4.0 gm of amberlite IR-120 (H-form). Subsequently, a solution of 3.0 gm (0.004 mol) of erythromycylamine in 10 ml of dioxane was added, and the reaction mixture was stirred for 4 hours more at room temperature. Thereafter, the ion exchanger was filtered off and washed with dioxane. The filtrate was evaporated, the oily residue was taken up in ether, the resulting solution was filtered, and petroleum ether was added until the mixture began to crystallize. The white, fine-crystalline product was suction-filtered off, washed with a mixture of ether and petroleum ether and dried. Yield: 2.5 gm (80% of theory); m.p. 100°-105° C (decomp.).

Elemental analysis: $C_{40}H_{74}N_2O_{12}S$; (807.11). Calculated: C, 59.52%; H, 9.24%; N, 3.47%; S, 3.96%. Found: C, 59.18%; H, 9.46%; N, 3.20%; S, 4.18%.

EXAMPLE 5

Carbethoxymethylthioacetaldehyde-erythromycylamine condensation product by method A An emulsion of 13 gm (0.055 mol) of carbethoxymethylthioacetaldehyde-diethylacetal in 130 ml of water was mixed with 55 gm of amberlite IR-120 (H-form), and the mixture was vigorously stirred at room temperature for 4 hours.

The resulting clear solution was filtered off from the ion exchanger, saturated with sodium chloride and extracted four times with 100 ml of ether. After drying over sodium sulfate, the solvent was distilled off. The aldehyde left as the residue was chromatographically pure and was used in the subsequent reaction without further purification. Yield: 7.6 gm (85% of theory) of carbethoxymethyl-thioacetaldehyde.

5.5 gm (0.0075 mol) of erythromycylamine and 7.5 gm (0.045 mol) of carbethoxymethyl-thioacetaldehyde were dissolved in 50 ml of methanol, and the solution was stirred at room temperature for 24 hours. After distilling off the solvent in vacuo, a dark brown oil remained behind, from which dark-colored byproducts were separated by treatment with a mixture of chloroform and ether. The solution was evaporated, the light-brown liquid residue was taken up in chloroform, and the resulting solution was de-colorized with charcoal and filtered. Ether was then added until the filtrate began to crystallize. The precipitated crystalline substance was suction-filtered off, washed with ether and dried. Yield: 6.2 gm (64% of theory); m.p. 150°-155° C (decomp.).

Elemental analysis: $C_{43}H_{78}N_2O_{14}S$; (879.14). Calculated: C, 58.75%; H, 8.94%; N, 3.19%; S, 3.65%. Found: C, 59.01%; H, 9.06%; N, 3.11%; S, 3.54%.

The following compounds were prepared analogous to Example 4 or 5:

a. Thioglycolaldehyde-erythromycylamine condensation product, m.p. 120°-125° C (decomp.).

b. Phenylthioacetaldehyde-erythromycylamine condensation product, m.p. 117°-120° C (decomp.).
c. p-Methylphenylthioacetaldehyde-erythromycylamine condensation product, m.p. 110°-112° C (decomp.).
d. o-Methoxyphenylthioacetaldehyde-erythromycylamine condensation product, m.p. 107°-110° C (decomp.).
e. Benzylthioacetaldehyde-erythromycylamine condensation product, m.p. 100°-105° C (decomp.).
f. (3-Phenyl)-propylthioacetaldehyde-erythromycylamine condensation product, m.p. 99°-103° C (decomp.).
g. Isopropylthioacetaldehyde-erythromycylamine condensation product, m.p. 100°-115° C (decomp.).
h. n-Pentylthioacetaldehyde-erythromycylamine condensation product, m.p. 107°-112° C (decomp.).
i. Cyclohexylthioacetaldehyde-erythromycylamine condensation product, m.p. 100°-105° C (decomp.).
j. (2-Hydroxy-ethyl)-thioacetaldehyde-erythromycylamine condensation product, m.p. 114°-117° C (decomp.).
k. (2-Diethylamino-ethyl)-thioacetaldehyde-erythromycylamine condensation product, m.p. 103°-108° C (decomp.).
l. (2-Carbomethoxy-ethyl)-thioacetaldehyde-erythromycylamine condensation product, m.p. 118°-121° C (decomp.).
m. Cyanomethylthioacetaldehyde-erythromycylamine condensation product, m.p. 120°-125° C (decomp.).

EXAMPLE 6

Acetylglycolaldehyde-erythromycylamine condensation product by method A

A mixture consisting of 2.3 gm (0.003 mol) of erythromycylamine, 1.1 gm (0.006 mol) of acetylglycolaldehyde-diethylacetal, 20 ml of dioxane, 2 ml of water and 12 gm of Dowex 50 W was stirred at room temperature. After 6 hours of stirring the ion exchanger was filtered off and washed with dioxane. The filtrate was evaporated, and the residue was purified by column chromatography (basic aluminum oxide, activity stage 3; chloroform/methanol = 4:1). The fraction with an $R_f$-value of 0.6 was evaporated and brought to crystallization by treatment with chloroform/ether. 2.4 gm of colorless crystals, m.p. 105°-110° C, was obtained.

Elemental analysis: $C_{42}H_{76}N_2O_{14}$; (833.04). Calculated: C, 60.55%; H, 9.20%; N, 3.36%. Found: C, 60.83%; H, 9.05%; N, 3.12%.

EXAMPLE 7

Benzoylglycolaldehyde-erythromycylamine condensation product by method A.

2.3 gm (0.003 mol) of erythromycylamine and 1.0 gm (0.006 mol) of benzoylglycolaldehyde were stirred in 60 ml of absolute dioxane at room temperature for 24 hours. After evaporation of the dioxane, the residue was taken up in chloroform, and the solution was mixed with ether. 0.8 gm of colorless crystals precipitated, which were dried at 20° C in vacuo. M.p. 110°-115° C (decomp.).

Elemental analysis: $C_{46}H_{76}N_2O_{14}$; (881.08). Calculated: C, 62.70%; H, 8.69%; N, 3.18%. Found: C, 62.95%; H, 8.42%; N, 3.35%.

The following compounds were prepared analogous to Example 6 or 7:

a. Butyrylglycolaldehyde-erythromycylamine condensation product, m.p. 65° C.
b. Phenylacetylglycolaldehyde-erythromycylamine condensation product, m.p. 70°-75° C.
c. N-Phenylcarbamoylacetaldehyde-erythromycylamine condensation product, m.p. 90°-95° C.
d. Dimethylcarboxamidomethoxyacetaldehyde-erythromycylamine condensation product, m.p. 160°-165° C.

EXAMPLE 8

Diethylphosphonoacetaldehyde-erythromycylamine condensation product by method A

A mixture consisting of 2.3 gm (0.003 mol) of erythromycylamine, 1.4 gm (0.006 mol) of diethylphosphonoacetaldehyde-dimethylacetal, 20 ml of dioxane, 2 ml of water and 12 gm of Dowex W 50 was stirred at room temperature. After 6 hours of stirring the ion exchanger was filtered off and washed with dioxane. Water was added to the filtrate until crystallization started. The white product was suction-filtered off, washed with aqueous dioxane and dried. Yield: 1.4 gm (52% of theory), m.p. 110°-113° C (decomp.).

Elemental analysis: $C_{43}H_{81}N_2O_{15}P$; (897.11). Calculated: C, 57.50%; H, 9.10%; N, 3.12%. Found: C, 57.21%; H, 9.19%; N, 3.08%.

EXAMPLE 9

Diethylphosphonoacetaldehyde-erythromycylamine condensation product by method A

A mixture consisting of 23 gm (0.03 mol) of erythromycylamine, 10 gm (0.055 mol) of diethylphosphonoacetaldehyde and 300 ml of absolute dioxane was stirred at room temperature for 24 hours. After evaporation of the solvent, the residue was taken up in 150 ml of hot acetonitrile, and the solution was mixed with 750 ml of water. Upon cooling 13 gm (43% of theory) of colorless crystals precipitated, which were dried at 80° C in vacuo. M.p. 110°-113° C (decomp.).

The compounds of the present invention have useful pharmacodynamic properties. More particularly, they exhibit antibacterial activity against gram-positive and gram-negative bacteria, such as *Staph.aureus* SG 511 and *E.coli*.

The antibacterial activity of the compounds of this invention was ascertained by means of the agar-diffusion test and the series dilution test in analogy to the respective methods described by P. Klein in "Bakteriologische Grundlagen der Chemotherapeutischen Laboratoriumspraxis", pages 53–76 and 87–109, published by Springer-Verlag, Stuttgart, Germany (1957).

For example, these tests showed that the following compounds still exhibited very effective antibacterial activity against *Staph.aureus* SG 511 at concentrations of 0.3 to 5 μgm/ml, and against *E.coli* at concentrations of 10 to 40 μgm/ml:

condensation product of erythromycylamine and methoxyacetaldehyde,
condensation product of erythromycylamine and glycolaldehyde,
condensation product of erythromycylamine and phenoxyacetaldehyde,
condensation product of erythromycylamine and acetylaminoacetaldehyde,
condensation product of erythromycylamine and N-(m,m',p-trimethoxybenzoyl)-aminoacetaldehyde, condensation product of erythromycylamine and o-toluylaminoacetaldehyde, condensation product of erythromycylamine and methylthioacetaldehyde, condensation product of erythromycylamine and (2-hydroxy)-ethoxyacetaldehyde, condensation product of erythromycylamine and cyclohexylthioacetaldehyde, condensation product of erythromycylamine and (2-methoxy)-ethoxyacetaldehyde, condensation product of erythromycylamine and benzylthioacetaldehyde, condensation product of erythromycylamine and (carbethoxy)-methoxyacetaldehyde, condensation product of erythromycylamine and butyrylglycolaldehyde, condensation product of erythromycylamine and dimethylcarboxamidomethoxyacetaldehyde, condensation product of erythromycylamine and diethylphosphonoacetaldehyde.

The acute toxicity of the compounds of this invention was determined in the mouse. After oral and subcutaneous application all of these compounds showed $LD_{50}$-values >1 gm/kg mouse.

For pharmaceutical purposes the compounds according to the present invention are administered to warm-blooded animals perorally or parenterally, but preferably perorally, as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antibacterial oral dosage unit of the compounds according to the present invention is from 0.83 to 8.3 mgm/kg body weight, preferably 1.6 to 4.2 mgm/kg body weight. The daily dose rate is from 8.3 to 66.7 mgm/kg, preferably 16.6 to 33.3 mgm/kg.

The following examples illustrate a few antibacterial pharmaceutical oral dosage unit compositions comprising a compound of the present invention as an active ingredient and represent the best modes contemplated of putting the invention into practical use. The parts are parts by weight unless otherwise specified.

EXAMPLE 10

TABLETS

The tablet composition is compounded from the following ingredients:

| | | |
|---|---:|---|
| Erythromycylamine-methoxyacetaldehyde condensation product | 100.0 | parts |
| Lactose | 63.0 | " |
| Potato starch | 50.0 | " |
| Polyvinylpyrrolidone | 5.0 | " |
| Magnesium stearate | 2.0 | " |
| Total | 220.0 | parts |

PREPARATION

The active ingredient, the lactose and the potato starch are intimately admixed with each other, the mixture is moistened with an aqueous 10% solution of the polyvinylpyrrolidone, the moist mass is granulated through a 1.5 mm-mesh screen, the granulate is dried at 45° C and again passed through the screen, and the dry granulate is admixed with the magnesium stearate. The resulting composition is compressed into 220 mgm-tablets, each of which contains 100 mgm of active ingredient.

EXAMPLE 11

COATED PILLS

The pill core composition is compounded from the following ingredients:

| | | |
|---|---:|---|
| Erythromycylamine-methylthioacetaldehyde condensation product | 100.0 | parts |
| Lactose | 30.0 | " |
| Corn starch | 30.0 | " |
| Gelatin | 3.0 | " |
| Cellulose, microcrystalline | 6.0 | " |
| Magnesium stearate | 1.0 | " |
| Total | 170.0 | parts |

PREPARATION

The active ingredient, the lactose and the corn starch are thoroughly admixed with each other, the mixture is moistened with an aqueous 12% solution of the gelatin, the moist mass is granulated through a 1.5 mm-mesh screen, and the granulate is dried at 45° C and again passed through a 1.0 mm-mesh screen. The dry granulate is admixed with the cellulose and the magnesium stearate, and the resulting composition is compressed into 170 mgm-pill cores, which are subsequently coated with a thin shell consisting essentially of a mixture of sugar and talcum, and finally polished with beeswax. Each pill contains 100 mgm of active ingredient.

EXAMPLE 12

SUSPENSION

The suspension is compounded from the following ingredients:

| | | |
|---|---:|---|
| Erythromycylamine-butyrylglycolaldehyde condensation product | 1.0 | parts |
| Sorbitol monopalmitate (Span 40) | 1.0 | " |
| Polyglycolether emulsifier (Cremophor O) | 2.0 | " |
| Cetyl stearyl alcohol (Lanette O) | 2.0 | " |
| Cetaceum | 1.0 | " |
| Decyloleate | 5.0 | " |
| Paraffin oil | 1.0 | " |
| Distilled water | 87.0 | " |
| Total | 100.0 | parts |

PREPARATION

The ingredients, with the exception of the active ingredient and the distilled water, are admixed with each other, the mixture is melted, and the molten mass is heated to 70° C and then emulsified in the distilled water at 70° C. The aqueous emulsion is cooled to 40° C, and the active ingredient is uniformly suspended therein with the aid of an immersion homogenizer. The finished suspension is cooled to room temperature. 100 gm of the suspension contain 1 gm of the active ingredient.

Any one of the other compounds of this invention may be substituted for the particular active ingredient in Examples 10 through 12. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An erythromycylamine-aldehyde condensation product of the formula

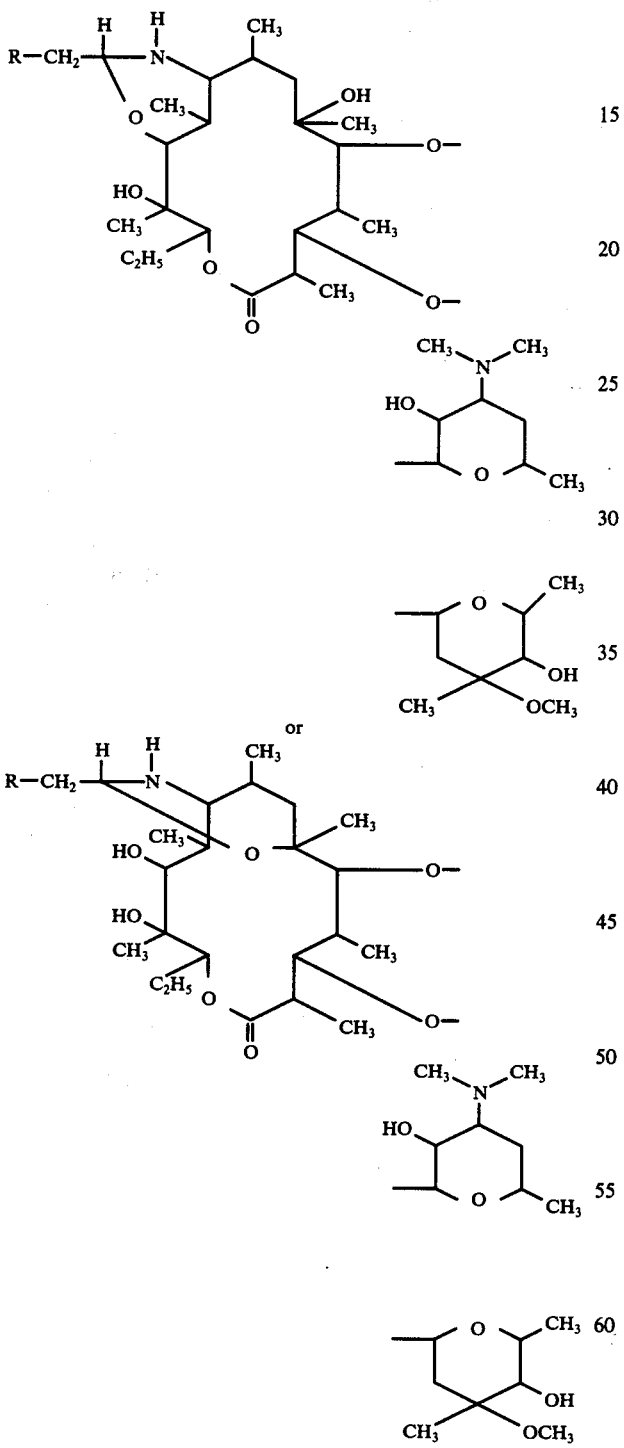

wherein R is hydroxyl; phenoxy; phenyl-(alkoxy of 1 to 3 carbon atoms); alkoxy of 1 to 4 carbon atoms; hydroxy-(alkoxy of 1 to 4 carbon atoms); (alkoxy of 1 to 3 carbon atoms)-(alkoxy of 1 to 4 carbon atoms); di(alkyl of 1 to 3 carbon atoms)amino-(alkoxy of 1 to 4 carbon atoms); (alkoxy of 1 to 3 carbon atoms)-carbonyl(alkoxy of 1 to 4 carbon atoms); mercapto; phenyl-mercapto, where the phenyl moiety is unsubstituted or methyl-, methoxy-, ethoxy-, isopropoxy- or propoxy-substituted; phenyl-(alkyl of 1 to 3 carbon atoms)-mercapto; (straight or branched alkyl of 1 to 5 carbon atoms)-mercapto; cyclohexyl-mercapto; hydroxy-(alkyl of 1 to 3 carbon atoms)-mercapto; di(alkyl of 1 to 3 carbon atoms)amino-(alkyl of 1 to 3 carbon atoms)-mercapto; (alkoxy of 1 to 3 carbon atoms)-carbonyl-(alkyl of 1 to 3 carbon atoms)-mercapto; cyano-(alkyl of 1 to 3 carbon atoms)-mercapto; —NR$_2$R$_3$, where R$_2$ and R$_3$, which may be identical to or different from each other, are each hydrogen, phenyl, phenyl-(alkyl of 1 to 3 carbon atoms), alkyl of 1 to 4 carbon atoms or, together with each other and the nitrogen atom to which they are attached, a 5- to 6-membered monocyclic heterocyclic ring which may contain an oxygen, sulfur or additional nitrogen atom;

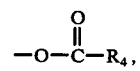

where R$_4$ is straight or branched alkyl of 1 to 5 carbon atoms, benzyl or phenyl; —NH—CO—R$_5$, where R$_5$ is straight or branched alkyl of 1 to 5 carbon atoms, mono- or dihalo-substituted-(alkyl of 1 to 5 carbon atoms), cyano-(alkyl of 1 to 5 carbon atoms), phenyl-(alkyl of 1 to 3 carbon atoms) where the phenyl moiety may be mono- or di- or trimethoxy- or mono- or di-halo-substituted and the alkyl moiety may be monohalo-substituted, phenoxy-(alkyl of 1 to 3 carbon atoms), phenyl-(alkenyl of 2 to 4 carbon atoms), phenyl or phenyl having one or more methyl, hydroxyl, methoxy, nitro or chloro substituents attached thereto; or R$_5$ is pyridyl; furyl; fluoro-furyl; thienyl; N-phenyl-carbamoyl;

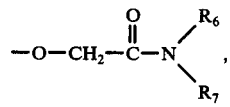

where R$_6$ and R$_7$, which may be identical to or different from each other, are each methyl, ethyl, propyl or isopropyl;

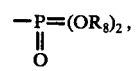

where R$_8$ is straight or branched alkyl of 1 to 5 carbon atoms; —NH—SO$_2$—R$_9$, where R$_9$ is alkyl of 1 to 4 carbon atoms or phenyl or (alkyl of 1 to 3 carbon atoms)-phenyl; or —SO$_2$—R$_{10}$, where R$_{10}$ is alkyl of 1 to 3 carbon atoms or phenyl or (alkyl of 1 to 3 carbon atoms)-phenyl;

or a non-toxic, pharmacologically acceptable acid addition salt thereof.

2. A compound of claim 1, which is the condensation product of erythromycylamine and methoxyacetaldehyde, or a non-toxic, pharmacologically acceptable acid addition salt thereof.

3. A compound of claim 1, which is the condensation product of erythromycylamine and glycolaldehyde, or a non-toxic, pharmacologically acceptable acid addition salt thereof.

4. A compound of claim 1, which is the condensation product of erythromycylamine and phenoxyacetaldehyde, or a non-toxic, pharmacologically acceptable acid addition salt thereof.

5. A compound of claim 1, which is the condensation product of erythromycylamine and acetylaminoacetaldehyde, or a non-toxic, pharmacologically acceptable acid addition salt thereof.

6. A compound of claim 1, which is the condensation product of erythromycylamine and N-(m,m',p-trimethoxybenzoyl-aminoacetaldehyde, or a non-toxic, pharmacologically acceptable acid addition salt thereof.

7. A compound of claim 1, which is the condensation product of erythromycylamine and o-toluylaminoacetaldehyde, or a non-toxic, pharmacologically acceptable acid addition salt thereof.

8. A compound of claim 1, which is the condensation product of erythromycylamine and methylthioacetaldehyde, or a non-toxic, pharmacologically acceptable acid addition salt thereof.

9. A compound of claim 1, which is the condensation product of erythromycylamine and (2-hydroxy-ethoxy)-acetaldehyde, or a non-toxic, pharmacologically acceptable acid addition salt thereof.

10. A compound of claim 1, which is the condensation product of erythromycylamine and (2-ethoxy)-acetaldehyde, or a non-toxic, pharmacologically acceptable acid addition salt thereof.

11. A compound of claim 1, which is the condensation product of erythromycylamine and diethylphosphonoacetaldehyde, or a non-toxic, pharmacologically acceptable acid addition salt thereof.

12. An antibacterial composition consisting essentially of an inert carrier and an effective antibacterial amount of a compound of claim 1.

13. The method of combatting bacterial infections in a warm-blooded host, which comprises perorally or parenterally administering to said host an effective antibacterial amount of a compound of claim 1.

* * * * *

UNITED STATES PATENT OFFICE
CERTIFICATE OF CORRECTION

Patent No. 4,048,306　　　　　　　　　Dated September 13, 1977

Inventor(s) ROLAND MAIER, EBERHARD WOITUN, BERND WETZEL, WOLFGANG REUTER, HANNS GOETH, UWE LECHNER It is certified that error appears in the above-identified patent and that said Letters Patent are hereby corrected as shown below:

Col. 8, line 13 "N-p-" should read -- N-o- --

Col. 6, line 18 "venyl" should read -- vinyl --

Col. 18, line 8 "(2-ethoxy)" should read

-- (2-methoxy-ethoxy) --

Signed and Sealed this

Twentieth Day of December 1977

[SEAL]

Attest:

RUTH C. MASON  
Attesting Officer

LUTRELLE F. PARKER  
Acting Commissioner of Patents and Trademarks

UNITED STATES PATENT AND TRADEMARK OFFICE

CERTIFICATE EXTENDING PATENT TERM
UNDER 35 U.S.C. § 156

PATENT NO.      :   4,048,306

ISSUED          :   September 13, 1977

INVENTOR(S)     :   Roland Maier et al.

PATENT OWNER    :   Boehringer Ingelheim GmbH

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,626 days from September 13, 1994, the original expiration date of the patent, with all rights pertaining thereto as provided by 35 U.S.C. § 156(b).

I have caused the seal of the Patent and Trademark Office to be affixed this 5th day of September 1997.

Bruce A. Lehman
Assistant Secretary of Commerce and
Commissioner of Patents and Trademarks